United States Patent
Öhman

(10) Patent No.: US 6,620,478 B1
(45) Date of Patent: Sep. 16, 2003

(54) CIRCULAR DISK CONTAINING MICROCHANNEL/MICROCAVITY STRUCTURES

(75) Inventor: Ove Öhman, Uppsala (SE)

(73) Assignee: Gyros AB, Uppsala (SE)

(*) Notice: Subject to any disclaimer, the term of this patent is extended or adjusted under 35 U.S.C. 154(b) by 0 days.

(21) Appl. No.: 09/625,022

(22) Filed: Jul. 25, 2000

Related U.S. Application Data

(62) Division of application No. 08/564,217, filed as application No. PCT/SE94/00584 on Jun. 14, 1994, now Pat. No. 6,126,765.

(30) Foreign Application Priority Data

Jun. 15, 1993 (SE) ................................................ 9302051

(51) Int. Cl.[7] .................................................. B32B 3/30
(52) U.S. Cl. ...................................... 428/64.1; 428/166
(58) Field of Search ................................ 428/64.1, 166

(56) References Cited

U.S. PATENT DOCUMENTS

| | | |
|---|---|---|
| 3,475,867 A | 11/1969 | Walsh |
| 3,538,744 A | 11/1970 | Karasek |
| 3,759,773 A | 9/1973 | Dwyer et al. |
| 4,957,582 A | 9/1990 | Columbus |
| 5,160,702 A | 11/1992 | Kopf-Sill et al. |
| 5,472,603 A | 12/1995 | Schembri |

FOREIGN PATENT DOCUMENTS

| | | |
|---|---|---|
| DE | 4128964 | 3/1993 |
| EP | 0 376 611 | 7/1990 |

*Primary Examiner*—Alexander S. Thomas
(74) *Attorney, Agent, or Firm*—Birch, Stewart, Kolasch & Birch, LLP

(57) ABSTRACT

The present invention relates to a circular disk, comprising two material layers that are joined together, wherein said disk contains microfluidic structures formed of a channel and/or cavity system defined between the two material layers, the recesses which correspond to the channels and/or cavities, respectively, being formed in one or both of opposed layer surfaces.

7 Claims, 1 Drawing Sheet

CIRCULAR DISK CONTAINING MICROCHANNEL/MICROCAVITY STRUCTURES

Figure 1A:
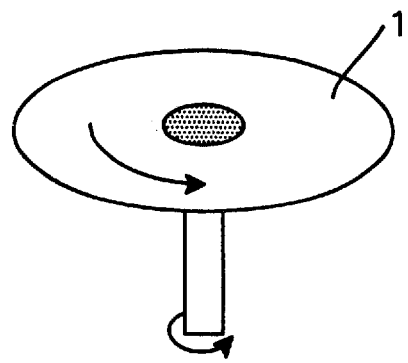

This application is a divisional of application Ser. No. 08/564,217, filed on Dec. 15, 1995, U.S. Pat. No. 6,126,765 application Ser. No. 08/564,217 is the national phase of phase of PCT International Application No. PCT/SE94/00584 filed on Jun. 14, 1994 under 35 U.S.C. §371. The entire contents of each of the above-identified applications are hereby incorporated by reference.

The present invention relates to the production of microchannel and microcavity systems, and more particularly to an improved method of bonding plane layers together in such production.

Microchannel or microcavity structures are used in inter alia chemical analytical techniques, such as electrophoresis and chromatography. In one type of such microfluidic structures, a channel and/or cavity system is defined between two plane material layers, the recesses which correspond to the channels and cavities, respectively, being formed in one or both of the opposed layer surfaces. The layers are usually bonded together by gluing. Alternatively, if the two layers consist of thermoplastic material, they may be fused together by the application of heat.

When very small channel dimensions are concerned, however, these conventional joining methods tend to deform the channel or cavity system to a great extent by partial clogging with glue or molten material.

The object of the present invention is to overcome this problem by providing a method which permits convenient bonding together of the material layers substantially without obstructing the channel or cavity system.

According to the invention, this is achieved by a method of forming a microchannel and/or microcavity structure by bonding together two elements (1, 2) having opposed plane surfaces of the same or different materials, one or both surfaces having open channels and/or cavities, characterized in that said bonding is effected by applying to one or both element surfaces (1, 2) a thin layer (3) of a solution of a material capable of fusing with and having a lower melting point than that of the material or materials of the two element surfaces (1, 2) in a solvent which substantially does not dissolve the element surface material or materials, removing the solvent, bringing the two elements (1, 2) together, and heating to a temperature where the dissolved material is caused to melt but not the element surface material or materials.

The invention is based on the concept that in order to bond together two planar element surfaces of the same or different materials, preferably thermoplastic, which surfaces when brought together define a channel and/or cavity system between them, there is applied to one or, preferably, both element surfaces a thin layer of another, preferably also thermoplastic, material dissolved in a solvent which does not dissolve the material of the two element surfaces. This dissolved material should, on one hand, be capable of being fused with the material(s) of the two surfaces on which it has been coated, and, on the other hand, melt at a lower temperature than the melting temperature of the element surface material or materials. After evaporation of the solvent, the two surfaces are brought together, e.g. by rolling, whereupon the assembly is heated to a temperature that melts the intermediate (preferably thermoplastic) material but not the material of the element surfaces for effecting joining of the two element surfaces.

The applied solution layer should, of course, have a very small thickness in relation to the width and depth of the channels and microcavities, respectively, which width and depth may be of the order of magnitude of 50 to 100 μm, for example.

When a thermoplastic material is used for the two material surfaces, this thermoplastic material is suitably closely related to the thermoplastic material responsible for the bonding of the channel/cavity structure. As an example of a suitable type of thermoplastic for the present purpose may be mentioned fluoroelastomers.

Suitable combinations of surface/bonding materials and solvents for practising the invention will readily be devised by the person skilled in the art guided by the present description.

Figure 1B:
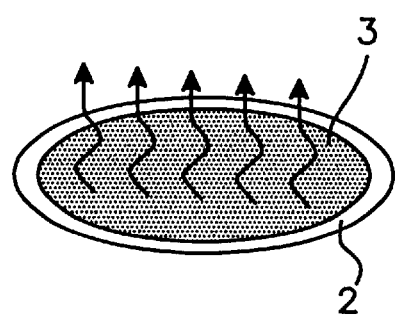
Figure 1C:
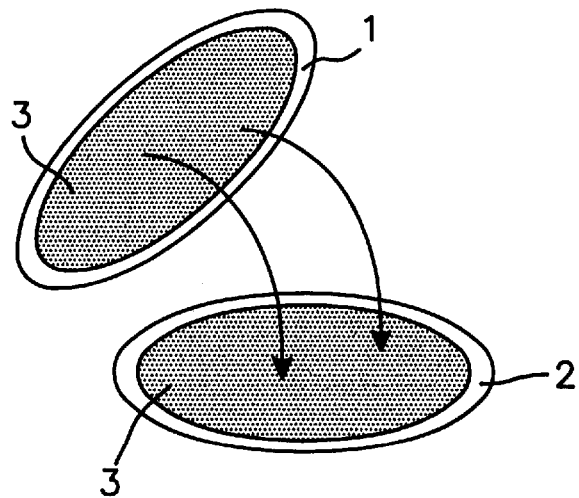
Figure 2:
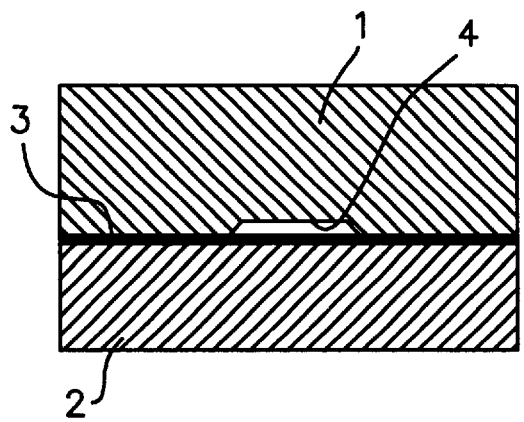

The carrying out of the process of the invention is illustrated schematically in the accompanying drawings, wherein FIGS. 1A to 1C show different substeps in the manufacture of a microfluidic structure, and FIG. 2 is a cross-section of the final product.

FIG. 1A shows a plate 1 provided with an open channel system (not shown), which plate together with an identical plate 2 without the channel system is intended to define a microchannel system between the two plates. For bonding the two plates together, which preferably are made of a thermoplastic material, e.g. a fluoroelastomer, a thin layer 3 of a, preferably closely related, thermoplastic material, e.g. a modified fluoroelastomer with a lower melting point, is first spun onto both plate surfaces. Then the solvent is baked off at an increased temperature (e.g. 135°C.), as is illustrated in FIG. 1B. The two plates treated in this way are then rolled together, as indicated in FIG. 1C, and are allowed to be bonded together for some time, e.g. 5 minutes. The completed microchannel structure is shown in FIG. 2. As may be seen from the latter figure, the two plates 1, 2, which are held together by the material layer 3, define a channel system 4 between them.

The following specific Example, which describes the production of a microchannel structure, illustrates the method of the invention further.

EXAMPLE

A polymer structure with closed straight channels having a height of 50 μm, a width of 250 μm and a length of about 80 mm was produced in the following manner.

A silicon mould having a surface relief structure corresponding to the desired channel geometry was manufactured in per se known manner. Thus, the surface of a silicon plate was first oxidzed at about 1100° C. to form an oxide layer of 8000 Å thickness. After washing, dehydration in an oven and priming with hexamethylsilane, a photoresist layer was spun onto the oxide layer and was stabilized by baking in an oven. A mask corresponding to the desired channel pattern was then placed on the plate surface, and the surface parts not covered by the mask were exposed to light. The exposed photoresist parts were then removed by developing solution to bare the oxide layer, and the remaining photoresist was hard-baked. The bared oxide was then etched with hydrofluoric acid/ammonium fluoride to expose the silicon (the backside of the plate being protected by resistant tape), whereupon the photoresist mask was removed by acetone. The oxide-free silicon surfaces were then etched with potassium hydroxide solution for a sufficient time to produce the desired etch depth. The resulting surface exhibited the desired channel pattern.

The silicon mould obtained was then pressed against a 2 mm thick film of Hostaflon TFB 7100 (refractive index about 1.36) at about 160° C. and 20 kp/cm². (Hostaflon is a thermoplastic fluoroelastomer sold by Hoechst AG, Germany). The resulting channel structure was bonded to a base layer in the form of a plane plate of the same material by spinning a thin layer of Hostaflon TFB X-7200 (having a lower melting point than that of Hostaflon TFB 7100) dissolved in propylmethylketone onto the base layer and the channel structure, which were then allowed to dry at 130° C. for 10 minutes. The channel structure and the base layer were then immediately rolled together, and the obtained sandwich was baked at about 140° C. for 10 minutes. The polymer structure produced in this way exhibited intact closed channels.

The invention is, of course, not restricted to the embodiment described above and specifically shown in the drawing, but many modifications and changes may be made within the scope of the general inventive concept as it is stated in the following claims.

What is claimed is:

1. A circular disk, comprising:
    two material layers that are joined together, wherein said disk contains microfluidic structures formed of a channel and/or cavity system defined between the two material layers, the recesses which correspond to the channels and/or cavities, respectively, being formed in one or both of opposed layer surfaces, wherein said material layers are joined together to form said disk substantially without obstructing the channel and/or cavity system, wherein at least one of said material layers is thermoplastic, and wherein said two material layers are joined together by an intermediate thermoplastic layer.

2. The circular disk according to claim 1, wherein the two layers are of the same material.

3. The circular disk according to claim 2, wherein the material is thermoplastic.

4. A circular disk, comprising:
    a first circular element;
    a second circular element; and
    an intermediate thermoplastic layer between said first circular element and said second circular element, wherein
    (a) said first and second elements are planar;
    (b) said first and second circular elements are joined together to form said disk,
    (c) said disk contains microfluidic structures formed of a channel and/or cavity system defined between the first and second circular elements,
    (d) recesses which correspond to the channels and/or cavities, respectively, are formed in one or both of opposed layer surfaces of said first and second circular elements,
    (e) said first and second elements are joined together by said intermediate thermoplastic layer, and
    (f) said first and second elements are joined together by the method comprising:
        (i) applying to the surface of one or both of said first and second circular elements a thin layer of a solution of dissolved thermoplastic material capable of fusing with, and having a lower melting point than that of the material or materials of the two element surfaces in a solvent which substantially does not dissolve the element surface material or materials;
        (ii) removing the solvent;
        (iii) bringing said surfaces of said first and second elements together to define a closed microchannel and/or microcavity system between them; and
        (iv) heating to a temperature where the dissolved thermoplastic material is caused to melt but not the element surface material or materials to bond said first and second elements together, whereby the first and second elements are bonded together substantially without obstructing the microchannel and/or microcavity system.

5. The circular disk according to claim 4, wherein said step of (i) applying comprises spinning said dissolved thermoplastic material onto the surface of one or both of said first and second circular elements.

6. The circular disk according to claim 5, wherein said spinning is accomplished by mounting each respective circular element on a shaft, and spinning said shaft.

7. A circular disk, comprising:
    two material layers that are joined together, wherein said disk contains microfluidic structures formed of a channel and/or cavity system defined between the two material layers, the recesses which correspond to the channels and/or cavities, respectively, being formed in one or both of opposed layer surfaces, wherein said material layers are joined together to form said disk substantially without obstructing the channel and/or cavity system, and wherein said two material layers are joined together by an intermediate thermoplastic layer.

* * * * *